United States Patent [19]

Durant et al.

[11] Patent Number: 4,578,388

[45] Date of Patent: Mar. 25, 1986

[54] UNSYMMETRICAL GUANIDINO, THIOUREIDO, ISOTHIOUREIDO AND NITROMETHYLENEAMINO DERIVATIVES

[75] Inventors: Graham J. Durant; Charon R. Ganellin, both of Welwyn Garden City, England

[73] Assignee: SmithKline & French Laboratories Limited, Welwyn Garden City, England

[21] Appl. No.: 509,563

[22] Filed: Jun. 30, 1983

Related U.S. Application Data

[62] Division of Ser. No. 272,811, Jun. 11, 1981, Pat. No. 4,405,621, which is a division of Ser. No. 70,950, Aug. 30, 1979, Pat. No. 4,301,165, which is a division of Ser. No. 941,836, Sep. 11, 1978, Pat. No. 4,197,305, which is a division of Ser. No. 836,626, Sep. 26, 1977, Pat. No. 4,137,319, which is a division of Ser. No. 678,564, Apr. 20, 1976, Pat. No. 4,070,472, which is a division of Ser. No. 542,971, Jan. 22, 1975, Pat. No. 3,968,227, reissued Sep. 12, 1978 as Re. 29,761.

[30] Foreign Application Priority Data

Feb. 7, 1974 [GB] United Kingdom ............... 5596/74

[51] Int. Cl.$^4$ .................. A61K 31/38; A61K 31/41; A61K 31/415; A61K 31/42; A61K 31/425; A61K 31/495; A61K 31/50; C07D 403/12; C07D 413/12; C07D 417/12

[52] U.S. Cl. ................................. 514/252; 548/187; 514/256; 548/203; 548/204; 514/269; 548/206; 548/213; 514/272; 548/225; 548/226; 514/274; 548/227; 548/228; 548/275; 548/229; 548/235; 514/359; 548/236; 514/362; 514/363; 514/365; 514/369; 514/370; 514/372; 514/374; 514/376; 514/377; 514/378; 514/380; 514/383; 514/384; 544/238; 544/239; 544/298; 544/333; 544/405; 548/127; 548/128; 548/134; 548/135; 548/136; 548/182; 548/183; 548/186

[58] Field of Search ............... 544/238, 239, 405, 333, 544/298; 548/127–128, 134–136, 182–183, 203–204, 186–187, 206, 213, 225–229, 235–236; 424/250, 251, 269, 270, 272; 514/252

[56] References Cited

U.S. PATENT DOCUMENTS

| | | | |
|---|---|---|---|
| 3,225,047 | 12/1965 | Partyka .............................. | 544/296 |
| 3,335,142 | 8/1967 | Hardy et al. ....................... | 544/296 |
| 3,337,552 | 8/1967 | Hirt .................................... | 544/296 |
| 3,622,596 | 11/1971 | Fischer et al. ..................... | 548/316 |
| 3,646,049 | 2/1972 | Hoff et al. ......................... | 548/112 |
| 3,917,626 | 11/1975 | Edwards ............................ | 546/265 |
| 3,968,227 | 7/1976 | Durant et al. .................. | 546/265 X |
| 4,034,101 | 7/1977 | Durant et al. .................. | 546/264 X |
| 4,062,967 | 12/1977 | Durant et al. ..................... | 514/397 |
| 4,070,472 | 1/1978 | Durant et al. .................. | 546/265 X |
| 4,137,234 | 1/1979 | Durant et al. ..................... | 548/187 |
| 4,137,319 | 1/1979 | Durant et al. ..................... | 514/340 |
| 4,151,289 | 4/1979 | Durant et al. ..................... | 514/400 |
| 4,154,844 | 5/1979 | Durant et al. ..................... | 514/363 |

FOREIGN PATENT DOCUMENTS

| | | |
|---|---|---|
| 1214239 | 4/1966 | Fed. Rep. of Germany . |
| 2215503 | 10/1972 | Fed. Rep. of Germany . |
| 405282 | 7/1966 | Switzerland . |
| 850483 | 10/1960 | United Kingdom . |

OTHER PUBLICATIONS

Conant et al., "The Chemistry of Organic Compounds" (N.Y., MacMillan, 1939), p. 264.

*Primary Examiner*—Donald G. Daus
*Assistant Examiner*—William A. Teoli, Jr.
*Attorney, Agent, or Firm*—Joan S. Keps; Richard D. Foggio; Alan D. Lourie

[57] ABSTRACT

The compounds are $C_2$-$C_8$ straight chain alkanes terminally substituted, symmetrically or unsymmetrically, by N-(N'-substituted guanidino), N-(N',N"-disubstituted guanidino), N-(N'-substituted thioureido), N-(nitromethylene amidino) or S-(N-substituted isothioureido) groups. Two compounds of the invention are 1,3-bis-[N'-(2-(5-methyl-4-imidazolylmethylthio)ethyl)-guanidino]propane and 1,3-bis-[S-(N-2-(5-methyl-4-imidazolylmethylthio)ethyl)isothioureido]propane. The compounds of this invention are inhibitors of H-2 histamine receptors.

12 Claims, No Drawings

UNSYMMETRICAL GUANIDINO, THIOUREIDO, ISOTHIOUREIDO AND NITROMETHYLENEAMINO DERIVATIVES

This is a division of application Ser. No. 272,811 filed June 11, 1981 now U.S. Pat. No. 4,405,621 which is a division of application Ser. No. 070,950 filed Aug. 30, 1979 Aug. 30, 1979 now U.S. Pat. No. 4,301,165, which is a division of application Ser. No. 941,836 filed Sept. 11, 1978 now U.S. Pat. No. 4,197,305, which is a division of application Ser. No. 836,626 filed Sept. 26, 1977 now U.S. Pat. No. 4,137,319, which is a division of application Ser. No. 678,564 filed Apr. 20, 1976 now U.S. Pat. No. 4,070,472, which is a division of application Ser. No. 542,971 filed Jan. 22, 1975 now U.S. Pat. No. 3,968,227 reissued as 05/843,399 Sept. 12, 1978 as Re. 29,761. Oct. 19, 1977.

This invention relates to new compounds using pharmacological activity. These compounds are inhibitors of H-2 histamine receptors. In addition, this invention relates to pharmaceutical compositions comprising these compounds and to methods of inhibiting H-2 histamine receptors by administering these compounds. The compounds of this invention can exist as the addition salts but, for convenience, reference will be made throughout this specification to the parent compounds.

Many of the physiologically active substances within the animal body, in the course of their activity, combine with certain specific sites known as receptors. Histamine is a compound which is believed to act in this way, but since the actions of histamine fall into more than one type, it is believed that there is more than one type of histamine receptor. The receptors involved in the type of action of histamine which is blocked by drugs commonly called "antihistamines", of which mepyramine is a typical example, have been designated as H-1 histamine receptors (Ash and Schild, Brit. J. Pharmac. Chemother 27 427. (1966). The receptors involved in the type of action of histamine which is not blocked by "antihistamines" such as mepyramine have been designated as H-2 histamine receptors and barimamide has been defined as an H-2 histamine receptor inhibitor (Black et al. Nature 236, 385 (1972)). Thus, H-2 histamine receptors may be defined as those histamine receptors which are not inhibited by mepyramine but are inhibited by burimamide.

Inhibitors of H-2 histamine receptors are utility in inhibiting actions of histamine which are not inhibited by "antihistamines". They are useful, for example, as inhibitors of gastric acid secretion.

The compounds of this invention are H-2 histamine receptor inhibitors. These compounds are represented by the following general formula

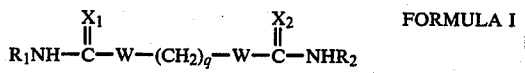

FORMULA I wherein $R_1$ and $R_2$, which may be the same or different, each represent a grouping of the structure shown in Formula II Het—$(CH_2)_m Z$—$(CH_2)_n$— FORMULA II wherein Het is a nitrogen containing 5 or 6 membered heterocyclic ring such as imidazole, pyridine, thiazole, isothiazole, oxazole, isoxazole, pyrazole, triazole, thiadiazole, pyrimidine, pyrazine or pyridazine which is optionally substituted by lower alkyl, hydroxyl, halogen or amino; Z is sulphur or a methylene group; m is 0, 1 or 2; n is 2 or 3 and the sum of m and n is 3,4, or when Y is other than hydrogen, methyl, or hydroxyl, 2; $X_1$ and $X_2$, which may be the same or different, are each sulphur, $CHNO_2$ or NY wherein Y is hydrogen, hudroxy, lower alkyl, cyano, $CONH_2$ or $SO_2R_3$; $R_3$ is lower alkyl, substituted or unsubstituted aryl, preferably phenyl or tolyl, trifluoromethyl or amino W is NH, and when $X_1$ and $X_2$ are NH W may also be sulphur: and q is an integer from 2 to 8 or a pharmaceutically acceptable acid addition salt thereof. It will be understood that the structure illustrated in Formula I is only one of several representations and that other tautomeric forms are also covered by the present invention.

Throughout the present specification and claims by the term 'lower alkyl' we mean an alkyl group containing from 1 to 4 carbon atoms.

In a preferred group of compounds $R_1$ and $R_2$ are the same. $R_1$ and/or $R_2$ are preferably Het-$CH_2S(CH_2)_2$- and it is particularly preferable that Het is imidazole, optionally substituted by methyl or halogen; thiazole; or isothiazole or pyridine optionally substituted by methyl, hydroxyl or halogen.

Likewise it is preferred that $X_1$ and $X_2$ be the same. Useful series of compounds are those wherein $X_1$ and $X_2$ are both sulphur, wherein $X_1$ and $X_2$ are both NY and Y is hydrogen or cyano, and wherein $X_1$ and $X_2$ are both $CHNO_2$.

It is preferred that q be from 2 to 4, particularly 3. Examples of specific compounds falling within the scope of the present invention are 1,2-bis-[N'-(2-(5-methyl-4-imidazolylmethylthio)ethyl) thioureido]-ethane 1,3-bis-[N'-(2-(5-methyl-4-imidazolylmethylthio)ethyl) thioureido]-propane 1,4-bis-[N'-(2-(5-methyl-4-imidazolylmethylthio)ethyl) thioureido]-butane 1,3-bis-[N'-(2-(5-methyl-4-imidazolylmethylthio)ethyl) guanidino]propane 1,3-bis-[N'-cyano-N"-(2-(5-methyl-4-imidazolylmethylthio) ethyl)guanidino]propane 1,3-bis-[S-(N-2-(5-methyl-4-imidazolylmethylthio)ethyl) isothioureido]propane The compounds of Formula I wherein W is NH, $R_2$ is the same as $R_1$, $X_1$ and $X_2$ are both $X_3$, $X_3$ being sulphur, $CHNO_2$, NH, NCN, or $NSO_2R_4$, $R_4$ being lower alkyl, substituted or unsubstituted aryl, preferably phenyl or tolyl, or trifluoromethyl, may be prepared by treating an excess (preferably two equivalents) of a compound of Formula III $R_1NHE$  FORMULA III wherein E is hydrogen or

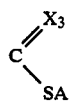

$X_3$ being as defined above and A being lower alkyl, with a compound of Formula IV $BNH)CH_2)_qNHB$ 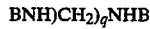 FORMULA IV wherein both the groups B are hydrogen when E is

and are

when E is hydrogen, $X_3$ and A being as defined above.

Preferably this reaction is carried out in a solvent, such as ethanol, isopropanol or pyridine. When $X_3$ is NCN or $NSO_2R_4$ the reaction may be modified by first adding a silver salt, such as silver nitrate, to the reactant bearing the

function, removing the silver alkyl mercaptide which is formed, and then adding the reacting amine.

Compounds of Formula III wherein E is

and $X_3$ is sulphur may be prepared from an amine of formula $R_1NH_2$ by successive reaction thereof with carbon disulphide and an alkylating agent, such as methyl iodide.

Compounds of Formula III wherein E is

and $X_3$ is $CHNO_2$, NCN, or $NSO_2R_3$ may be prepared by treating a compound of Formula V

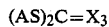                      FORMULA V wherein $X_3$ is $CHNO_2$, NCN, or $NSO_2R_4$ and A is alkyl, with an equivalent amount of an amine of formula $R_1NH_2$. This reaction is conveniently carried out in a solvent such as ethanol.

The compounds of Formula III wherein E is

and $X_3$ is NH are conveniently prepared by alkylating a thiourea of formula $R_1NHCSNH_2$. These thioureas may be prepared by treating an amine of formula $R_1NH_2$ with benzoyl isothiocyanate, and hydrolysing the product under alkaline conditions.

The compounds of Formula IV wherein both the groups are

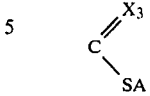

may be prepared from the corresponding diamines by methods similar to those described above for the preparation of compounds of Formula III wherein Y is

Mild acid hydrolysis of the compounds of Formula I wherein $X_1$ and $X_2$ are both NCN yields the compounds of Formula I wherein $X_1$ and $X_2$ are both $NCONH_2$. Acid hydrolysis of the compounds of Formula I wherein $X_1$ and $X_2$ are both NCN yields the compounds of Formula I wherein $X_1$ and $X_2$ are both NH.

The compounds of Formula I wherein $X_1$ and $X_2$ are both $NHSO_2NH_2$ may be prepared from the corresponding compounds of Formula I wherein W is NH and $X_1$ and $X_2$ are both NH by reaction of the latter compounds with N-piperidylsulphamide. This reaction is conveniently carried out in boiling ethanol.

The above methods of synthesis may be modified to produce those compounds wherein W=NH and $X_1$ and $X_2$ and/or $R_1$ and $R_2$ are different. In this case the starting material is conveniently the diamine of Formula IV, wherein both the groups B are hydrogen, which is first treated with a suitable reagent to form a monoprotected diamine of Formula VI $QNH(CH_2)_qNH_2$           FORMULA VI wherein q has the above significance and Q is a suitable protecting group e.g., an acid labile protecting group such as benzoyl or formyl. Reaction of this compound with one equivalent of a compound of Formula III wherein E is

gives the compound of Formula VII

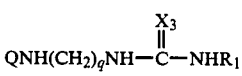           FORMULA VII wherein $R_1$, $X_3$, Q and q have the above significance. Treatment of this compound with acid followed by reaction with a substance of Formula VIII

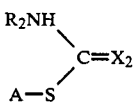           FORMULA VIII wherein A, $R_2$ and $X_2$ have the above significance and $R_2$ and/or $X_2$ are not identical to $R_1$ and/or $X_1$ in Formula VII results in the required compound of Formula I wherein $R_1$ and $R_2$ and/or $X_1$ and $X_2$ are different. Alternatively, the amine of Formula VI may be converted into a compound of Formula IX

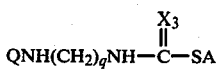
FORMULA IX wherein Q, q, $X_3$ and S have the above significance, by the general methods described above for the preparation of compounds of Formula IV wherein E is

Treatment of a compound of Formula IX with an amine of formula $R_1NH_2$, $R_1$ being as defined above, gives a compound of Formula VII which may be converted into a compound of Formula I by successive treatment with acid and a compound of Formula VIII as described above.

It will be appreciated that the above processes for the production of compounds of Formula I wherein W is NH involve the reaction between a compound of Formula III and a compound of Formula X $$BNH(CH_2)_qNHG \quad \text{FORMULA X}$$

wherein B is hydrogen when E is

and B is $$\overset{X_3}{\underset{SA}{C{\nearrow}{\searrow}}}$$

when E is hydrogen, A being lower alkyl and $X_3$ being sulphur, $CHNO_2$, NH, NCN or $NSO_2R_4$, $R_4$ being lower alkyl, substituted or unsubstituted aryl or trifluoromethyl, q is as defined in Formula I and G is B or a group $-CX_2NHR_2$ wherein $X_2$ and $R_2$ are as defined in Formula I.

The compounds of Formula I wherein $X_1$ and/or $X_2$ are NY and Y is hydroxy or lower alkyl may be prepared from the corresponding thiourea of Formula I wherein $X_1$, and/or $X_2$ is sulphur, and neither $X_1$ nor $X_2$ are NH by alkylating the thiourea, e.g., by treatment with hydrogen chloride in methanol or methyl iodide, and then treating the resulting compound with hydroxylamine or a lower alkylamine, respectively.

The compounds of Formula I wherein $X_1$ and/or $X_2$ are NCN may alternatively be prepared from the corresponding thiourea of Formula I wherein $X_1$ and/or $X_2$ is sulphur, and neither $X_1$ nor $X_2$ are NH, by alkylation and treatment of the product with cyanamide and a strong base such as potassium t-butoxide.

The compounds of Formula I wherein $X_1$ or $X_2$ are N.CN may also be prepared from the corresponding compounds of Formula I wherein $X_1$ or $X_2$ are sulphur by reaction of the latter with a heavy metal salt of cyanamide such as lead, mercury or cadmium cyanamide in a solvent such as acetonitrile and/or dimethylformamide.

The compounds of Formula I wherein W is sulphur and $X_1$ and $X_2$ are both NH may be prepared by alkylating a thiourea of Formula $R_1NHCSNH_2$ wherein $R_1$ is as defined in Formula I with a dihalo compound of formula $Hal—(CH_2)_q—Hal$, wherein Hal represents chlorine, bromine or iodine. Preferably the reaction is carried out on an acid addition salt of the thiourea, Hal is bromine and the reaction is carried out in a suitable solvent such as ethanol.

The compounds of Formula I are inhibitors of H-2 histamine receptors, that is they are inhibitors of the actions of histamine which are not blocked by "antihistamines" such as mepyramine but are blocked by burimamide. For example, the compounds of this invention have been found to inhibit selectively the histamine-simulated secretion of gastric acid from the lumen-perfused stomachs of rats anaesthetized with urethane, at doses of from 0.5 to 256 micromoles per kilogram intravenously. This procedure is described in the above mentioned paper of Ash and Schild. Also, the activity of these compounds as H-2 histamine receptor inhibitors is demonstrated by their antagonism to other actions of histamine which, according to the above mentioned paper of Ash and Schild, are not mediated by H-1 histamine receptors. For example, the H-2 histamine receptor inhibitory activity of the compounds of this invention is demonstrated by antagonism of the actions of histamine in stimulating isolated guinea pig atrium and inhibiting contractions in the isolated rat uterus.

The compounds of this invention inhibit the secretion of gastric acid stimulated by pentagastrin or by food. The level of activity found for the compounds of the present invention is illustrated by the effective dose range in the anaesthetised rat, as mentioned above of from 0.5 to 256 micromoles per kilogram, intravenously.

Many of the compounds of the present invention produce a 50% inhibition in this test at a dose of from 1 to 10 micromoles per kilogram.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol or by the use of ion exchange resins to form the required salt either directly from the base or from a different addition salt. Pharmaceutical compositions comprising a pharmaceutical carrier and a compound of Formula I or a pharmaceutically acceptable acid addition salt thereof and methods of inhibiting H-2 histamine receptors which comprise administeing a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche r lozenge. The amount of solid carrier will vary widely but preferably will be from about 25 mg. to about 1 g. If a liquid carrier is used, the preparation may be in the form of a syrup, emulsion, soft gelatin capsule, sterile injectable liquid such as in an ampoule, or an aqueous or non-aqueous liquid suspension.

The pharmaceutical compositions are prepared by conventional techniques, involving procedures such as mixing, granulating and compressing or dissolving the ingredients as appropriate to the desired preparation.

The active ingredient will be present in the compositions in an effective amount to inhibit H-2 histamine receptors. The route of administering may be orally or parenterally. Preferably, each dosage unit will contain the active ingredient in an amount of from about 50 mg to about 250 mg.

The active ingredient will preferably be administered in equal doses one to six times per day. The daily dosage regimen will preferably be from about 150 mg to about 1500 mg.

Other pharmacologically active compounds may in certain cases be included in the composition. Advantageously the composition will be made up in a dosage unit form appropriate to the desired mode of administration, for example as a tablet, capsule or injectable solution.

The invention is illustrated but in no way limited by the following examples wherein all temperatures are in degrees Centigrade:

EXAMPLE 1

1,2-bis-[N'-(2-(5-methyl-4-imidazolylmethylthio)ethyl) thioureido]ethane.

(a) A solution of 4-methyl-5-((2-aminoethyl)thiomethyl)imidazole (10.2 g) in ethanol (75 ml) was added slowly, with stirring, to carbon disulphide (200 ml). The mixture was set aside overnight at room temperature and the solid formed was collected and recrystallised from aqueous isopropyl alcohol to afford N-[2-((5-methyl-4-imidazolyl)-methylthio)ethyl]dithiocarbamic acid (9.8 g)., m.p. 127–129°.

(Found: C, 38.6 H, 5.5: N, 16.7: $C_8H_{13}N_3S_3$ requires: C, 38.8 H, 5.3 N, 17.0%).

(b) Methyl iodide (4.0 g) was added to a suspension of the dithiocarbamic acid (7.0 g) inn methanol (100 ml). After stirring at room temperature for 1.5 hours, a solution was obtained. Concentration followed by recrystallisation of the residue from isopropyl alcohol-ether gave S-methyl-N-[2-((5-methyl-4-immidazolyl)methylthio)ethyl]-dithiocarbamate hydriodide (8.6 g), m.p. 167–169°.

(Found: C, 27.7: H, 4.0: N, 10.8: I, 32.9: $C_9H_{15}N_3S_3.HI$ requires: C, 27.8: H, 4.1: N, 10.8: I, 32.6%).

(c) A solution of the above hydriodide (5.5 g) in absolute ethanol (60 ml) was added to a solution of sodium (0.325 g) in ethanol (100 ml). Following filtration, a solution of 1,2-diaminoethane (0.424 g) in ethanol (30 ml) was added to the filtrate which was heated under reflux for 24 hours. Following concentration, the residual oil was purified by repeated reprecipation from isopropanol with water and from isopropanol with ether. Finally chromatographic purification on a column of silica gel with ethyl acetate-ethanol (3:1) as eluant and final precipitation from isopropanol-ether gave the title compound as a colourless low melting solid, containing approximately 4.5% diethyl ether.

The NMR spectrum of a solution in $^2H_6$ dimethyl sulphoxide, recorded at 60 mHZ showed the following resonances:

| | | |
|---|---|---|
| —N$\underline{H}$—CS—N$\underline{H}$—: | multiplet at δ7.7 | integral, 6.0 protons: calculated, 6.0 protons. |
| imidazole-2-$\underline{H}$: | singlet at δ7.48 | |
| imidazole-C$\underline{H}_2$—: | singlet, at δ3.68 | integral, 12.4 protons: calculated, 12.0 protons. |
| —C$\underline{H}_2$—NH—CS—NH—C$\underline{H}_2$: | multiplet at δ3.5 | |
| —CH$_2$C$\underline{H}_2$S—: | multiplet, at δ2.62 | integral could not be measured |
| imidazole-C$\underline{H}_3$: | singlet, at δ2.13: | the integral was used as the internal standard, equal to 6.0 protons |

The spectrum also showed the presence of 4.5% w/w diethyl ether.

(Found: C, 45.6 H, 6.7: $C_{18}H_{30}N_8S_4$+4.5% $C_4H_{10}O$ requires: C, 45.3 H, 6.5%).

EXAMPLE 2

1,3-bis-[N'-(2-(5-methyl-4-imidazolyl methylthio)ethyl) thioureido]propane

S-Methyl-N'-[2-(5-methyl-4-imidazolyl) methylthio)ethyl]dithiocarbamate hydriodide (7.8 g) was converted into the free base with sodium (0.46 g) in ethanol. Reaction with 1,3-diaminopropane (0.74 g) and purification by the method described in Example 1 gave the product which was further purified by successive treatment of a solution in methanol-water with cationic and anionic exchange resins. Following precipitation from isopropanol-ether, the title compound was obtained as a colourless low melting solid containing approximately 4.5% diethyl ether.

The NMR spectrum of a solution in $^2H_6$ dimethyl sulphoxide recorded at 60 mHZ showed the following resonances.

| | | |
|---|---|---|
| —N$\underline{H}$—CS—N$\underline{H}$—: | triplet δ7.62 | integral, 7.0 protons: calculated 6.0 protons. |
| imidazole-2$\underline{H}$: | singlet δ7.42 | |
| imidazole-C$\underline{H}_2$: | singlet, δ3.67 | integral 13.0 protons(including H$_2$O in NMR solvent): calculated 12.0. |
| C$\underline{H}_2$NH—CSNH—C$\underline{H}_2$: | multiplet, δ3.5 | |

| | | |
|---|---|---|
| CH₂—CH₂—S: | triplet δ2.60 | integral 5.0 protons(including DMSO-d₅): calculated 4.0. |
| imidazole-CH₃: | singlet δ2.13: | The integral was used as the internal standard, equal to 6.0 protons. |
| CH₂CH₂CH₂: | multiplet δ1.7: | integral 2.0 protons: calculated 2.0 protons. |

The spectrum also showed the presence of 4.5% weight/weight diethyl ether.

(Found: N, 21.7: S, 24.6; $C_{19}H_{32}N_8S_4 + 4.5\%$ $C_4H_{10}O$ requires: N, 21.4: S, 24.5%)

EXAMPLE 3

1,4-bis-[N'-(2-(5-Methyl-4-imidazolylmethylthio)ethyl) thioureido]butane

S-Methyl-N'-[2-(5-methyl-4-imidazolyl)methylthio)ethyl]dithiocarbamate hydriodide (5.5 g) was converted into the free base with sodium in ethanol. Reaction with 1,4-diaminobutane (0.63 g) and subsequent purification by the method described in Example 1 afforded the title compound as a low-melting colourless solid containing approximately 5.9% diethyl ether.

The NMR spectrum of a solution in $^2H_6$ dimmethyl sulphoxide recorded at 60 mHZ showed the following resonances.

| | | |
|---|---|---|
| —NH—CS—NH—: | multiplet, δ7.6 | integral 5.8 protons: calculated, 6.0 protons. |
| imidazole-2H: | singlet, δ7.47 | |
| imidazole-CH₂: | singlet, δ3.69 | integral 12.6 protons: calculated, 12.0 protons. |
| CH₂CH₂N—: | multiplet, δ3.5 | |
| CH₂CH₂S: | triplet, δ2.63 | The integral could not be measured. |
| CH₃—Imidazole: | singlet, δ2.15: | The integral was used as the internal standard, equal to 6.0 protons. |
| CH₂—(CH₂)₂—CH₂: | multiplet, δ1.5 | integral 4.2 protons calculated 4.0 protons |

The spectrum also showed the presence of 5.9% weight/weight diethyl ether.

(Found: C, 47.6: H, 7.2; $C_{20}H_{34}N_8S_4 + 5.9\%$ $C_4H_{10}O$ requires: C, 47.7 H, 7.1%)

EXAMPLE 4

1,5-bis[N'-(2-(5-Methyl-4-imidazolylmethylthio)ethyl) thioureido]pentane

The reaction of S-methyl-N'-[2-(5-methyl-4-imidazolyl) methylthio)ethyl]dithiocarbamate with 1,5-diaminopentane by the method described in Example 1 gave the title compound as an amorphous powder which contained residual ether and water.

(Found: C, 47.5: H, 7.2 N, 19.9: S, 23.3 $C_{21}H_{36}N_8S_4 + 2\%$ $C_4H_{10}O$ $+2\%$ $H_2O$ requires: C, 47.1: H, 7.1: N, 20.3: S, 23.3%).

The NMR spectrum of a solution in $^2H_6$ dimethyl sulphoxide recorded at 60 mHZ showed the following resonances.

| | | |
|---|---|---|
| —NH—CS—NH—: | multiplet, 435-465 Hz | integral 5.3 protons calculated, 6.0 protons |
| imidazole-2H: | singlet, δ7.47 | |
| imidazole-CH₂: | singlet, δ3.68 | integral 12.3 protons calculated 12.0 protons |
| CH₂CH₂S + CH₂CH₂N: | multiplet, 185-235 Hz | |
| CH₂—CH₂—S: | multiplet, 140-175 Hz | integral 4.5 protons (including DMSO-d₅) calculated 4 protons |
| CH₃—Imidazole: | singlet, δ2.15: | The integral was used as the internal standard equal to 6 protons. |
| CH₂(CH₂—CH₂)₂NH | multiplet, 70-110 Hz | Integral 5.3 protons calculated 6.0 protons |

EXAMPLE 5

1,3-bis-[N'-(2-(5-Methyl-4-imidazolylmethylthio)ethyl)-guanidino]propane (i) A solution of N-[2-((5-methyl-4-imidazolyl)methylthio) ethyl]thiourea (2.29 g) and methyl iodide (1.56 g) in methanol (5 ml) was kept at room temperature for 18 hours affording S-methyl-N-[2-((5-methyl-4-imidazolyl)methylthio)ethyl]thiouronium iodide (2.3 g), m.p. 128–131°. The iodide was converted into the corresponding sulphate by ion-exchange on an ion-exchange resin (IRA 401) in the sulphate form.

(ii) 1,3-Diaminopropane (0.37 g) was added to a solution of S-methyl-N-[2-((5-methyl-4-imidazolyl)methylthio)ethyl]thiouronium sulphate (2.93 g) in water (10 ml) and the mixture was heated under reflux for 2 hours. Following concentration the residue was converted into the picrate with an aqueous solution of sodium picrate. Recrystallisation from ethanol afforded the title compound as the dipicrate (1.1 g) m.p. 114–6°.

(Found: C, 40.3: H, 4.2 N, 23.7: S, 6.9; $C_{19}H_{36}N_{10}S_2.2 C_6H_3N_3O_7$ requires: C, 40.3; H, 4.4; N, 24.2; S, 6.9%).

The dipicrate was dissolved in aqueous methanol and treated with ion-exchange resin IRA 400 (Cl−) to afford the dihydrochloride
(Found: Cl, 12.8% $C_{19}H_{36}N_{10}S_2 \cdot 2HCl$ requires: Cl, 13.1%).

EXAMPLE 6

1,2-bis-[N'-(2-(5-Methyl-4-imidazolylmethylthio)ethyl) guanidino]ethane

The reaction of 1,2-diaminoethane (0.60 g) with S-methyl-N-[2-((5-methyl-4-imidazolyl)methylthio)ethyl]thiouronium sulphate (5.86 g) by the method described in Example 5 afforded the title compound which was isolated as the dipicrate (3.5 g), m.p. 201–203°.
(Found: C, 39.5; H, 4.3 N, 24.2 S, 6.9; $C_{18}H_{34}N_{10}S_2 \cdot 2 C_6H_3N_3O_7$ requires: C, 39.6; H, 4.2; N, 24.6; S, 7.0%).

EXAMPLE 7

1,5-bis-[N'-(2-(5-Methyl-4-imidazolylmethylthio)ethyl) guanidino]pentane

The reaction of 1,5-diaminopentane (0.43 g) with S-methyl-N-[2-((5-methyl-4-imidazolyl)methylthio)ethyl]thiouronium sulphate (2.52 g) by the method described in Example 5 afforded the title compound which was isolated as the dipicrate (1.8 g) m.p. 115–120°.

EXAMPLE 8

1,3-bis-[N'-Cyano-N''-(2-(5-methyl-4-imidazolylmethylthio) ethyl)guanidino]propane (a) A mixture of 1,3-bis-[N-cyano-S-methyl-isothioureido]propane (1.67 g) and 5-methyl-4-(2-aminoethyl-)imidazole (2.36 g) in anhydrous pyridine (40 ml) was heated under reflux for 8 hours. Following concentration and trituration with acetonitrile-water (2:1) the product was chromatographed on a column of silica with elution by a mixture of chloroform (85 parts) and methanolic ammonia (15 parts) to yield the title compound.

The NMR spectrum of a solution in $^2H_6$ dimethyl sulphoxide showed the following resonances.
imidazole-2H̲; Singlet,δ 7.56
N-H̲; multiplet,δ 7.22
imidazole-CH̲$_2$; singlet,δ 3.68
CH$_2$CH̲$_2$NH; multiplet,δ 3.25
CH$_2$CH̲$_2$S; multiplet,δ 2.65
CH$_3$-imidazole; singlet,δ 2.16
CH̲$_2$CH$_2$CH$_2$; multiplet,δ 1.75

(b) Lead cyanamide (3.0 g) was added to 1,3-bis-[N'-(2-(5-methyl-4-imidazolylmethylthio)ethyl)thioureido] propane (2.5 g) in acetonitrile. Dimethylformamide was added and the mixture was stirred and boiled under reflux for 24 hours. The mixture was filtered, concentrated and purified by chromatography to give the title compound.

(c) A mixture of 1,3-bis-[N'-(2-(5-methyl-4-imidazolyl-methylthio)ethyl]thioureido)propane (10.3 g) 55% hydriodic acid (12.2 ml) methyl iodide (5.3 ml) and methanol was boiled under reflux for 4 hours and, evaporated to dryness to give 1,3-bis-[S-methyl-N'-(2-(5-methyl-4-imidazolyl methylthio)-ethyl]isothioureido)-propane tetrahydriodide. This intermediate (2.05 g) was treated with potassium t-butoxide (1.5 g) and cyanamide (0.5 g) in anhydrous t-butanol and the mixture was boiled under reflux overnight, filtered, and purified by chromatography to give the title product.

EXAMPLE 9

1,2-bis-[S-(N-2-(5-Methyl-4-imidazolylmethylthio)ethyl) isothioureido]ethane tetrahydrobromide A solution of N-[2-(5-methyl-4-imidazolyl)methylthio)ethyl]thiourea (3.45 g) in isopropyl alcohol (25 ml) was cooled and 48% aqueous hydrobromic acid (2.54 g) added. The hydrobromide salt was precipitated with excess ether and dissolved in ethanol (25 ml). 1,2-Dibromoethane (1.5 g) was added and the solution obtained was heated under reflux for 24 hours. Concentration and crystallisation from methanol-isopropyl alcohol afforded the title compound (2.2 g) m.p. 215–217°.
(Found: C, 26.7; H, 4.1; N, 13.8; S, 15.8; Br, 39.6; $C_{18}H_{30}N_8S_4 \cdot 4$ HBr requires: C, 26.7; H, 4.2; N, 13.8; S, 15.8; Br, 39.4%).

EXAMPLE 10

1,3-bis-[5-(N-2-(5-Methyl-4-imidazolylmethylthio)ethyl) isothioureido]propane

The reaction of N-[2-(5-methyl-4-imidazolyl)methylthio)ethyl]thiourea hydrobromide (from 3.45 g of the thiourea) with 1,3-dibromopropane by the method described in Example 9 afforded the title compound which was isolated as its tetrapicrolonic acid salt (4.75 g), m.p. 165–167° (from nitromethane-ethanol).
(Found: C, 45.2; H, 4.3; N, 21.5; S, 7.8%. $C_{19}H_{32}N_8S_4 \cdot 4 C_{10}H_8N_4O_5$ requires: C, 45.5; H, 4.1; N, 21.6; S, 8.2%).

The tetrapicrolonate salt was suspended in aqueous methanol and treated with ion-exchange resin IRA 401 (Cl−form) and the suspension stirred for 3 hours. Concentration afforded the tetrahydrochloride (0.9 g),m.p. approx. 110°
(Found: C, 35.1; H, 6.0; $C_{19}H_{32}N_8S_4 \cdot 4$ HCl requires: C, 35.3 H, 5.9%)

EXAMPLE 11

1,4-bis-[S-(N-2-(5-Methyl-4-imidazolylmethylthio)ethyl) isothioureido]butane tetrahydrobromide The reaction of N-[2-(4-methyl-5-imidazolyl)methylthio)ethyl]thiourea hydrobromide (from 3.25 g of the thiourea) with 1,4-dibromobutane (1.62 g) by the method described in Example 9 afforded the title compound (3.8 g), m.p. 185–187° (from ethanol)
(Found: C, 28.7; H, 4.6; N, 13.4; Br, 38.2; S, 15.1; $C_{20}H_{34}N_8S_4 \cdot 4$ HBr requires: C, 28.7; H, 4.6; N, 13.4; S, 38.1; S, 15.3%).

EXAMPLE 12

When 1,8-diaminooctane is substituted for 1,2-diaminoethane in the procedure of Example 1 (c), 1,8-bis-[N'-2-(5-methyl-4-imidazolylmethylthio)ethyl)thioureido]octane is produced. When 1,8-diaminooctane is substituted for 1,3-diaminopropane in the procedure of Example 5(ii), 1,8-bis-[N'-(2-(5-methyl-4-imidazolylmethylthio)ethyl)guanidino]octane is produced.

When 1,6-diaminohexane is substituted for 1,2-diaminoethane in the procedure of Example 1(c), 1,6-bis-[N'-(2-(5-methyl-4-imidazolylmethylthio)ethyl)thioureido]hexane is produced. When 1,6-diaminohexane is substituted for 1,3-diaminopropane in the procedure of Example 5(ii), 1,6-bis-[N'-(2-(5-methyl-4-imidazolylmethylthio)ethyl)guanidino]hexane is produced.

EXAMPLE 13

When 1,6-dibromohexane or 1,8-dibromooctane are substituted for 1,2-dibromoethane in the procedure of Example 9 the products are 1,6-bis-[S-(N-2-(5-methyl-4-imidazolylmethylthio)ethyl)isothioureido]hexane and 1,8-bis-[S-(N-2-(5-methyl-4-imidazolylmethylthio)ethyl)isothioureido]octane, respectively.

EXAMPLE 14

Reaction of 4-methyl-5-((2-aminoethyl)thiomethyl)imidazole with
(a) N-methanesulphonyliminodithiocarbonic acid dimethyl ester
(b) N-p-toluenesulphonyliminodithiocarbonic acid dimethyl ester
(c) N-benzenesulphonyliminodithiocarbonic acid dimethyl ester
(d) N-trifluoromethanesulphonyliminodithiocarbonic acid dimethyl ester in ethanol at room temperature gave the corresponding S-methyl-N-[2-((5-methyl-4-imidazolyl)methylthio)ethyl]-N'-sulphonylthiouronium derivatives which were treated with 1,3-diaminopropane according to the general procedure of Example 5(ii) to give
(a) 1,3-bis-[N'-methanesulphonyl-N''-(2-(5-methyl-4-imidazolylmethylthio)ethyl)-guanidino]propane
(b) 1,3-bis-[N'-toluenesulphonyl-N''-2-(5-methyl-4-imidazolylmethylthio)ethyl)-guanidino]propane
(c) 1,3-bis-[N'-benzenesulphonyl-N''-(2-(5-methyl-4-imidazolylmethylthio)ethyl)-guanidino]propane
(d) 1,3-bis-[N'-trifluoromethanesulphonyl-N''-(2-(5-methyl-4-imidazolylmethylthio)ethyl)-guanidino]propane

EXAMPLE 15

1,3-bis-[N'-Sulphamyl-N''-(2-(5-methyl-4-imidazolylmethylthio) ethyl)guanidino]propane 1,3-bis-[N'-(2-(5-Methyl-4-imidazolylmethylthio)ethyl)guanidino]propane dihydrochloride (2.7 g) was added to a solution of sodium (0.46 g) in ethanol (50 ml) and the mixture was warmed and stirred for 0.5 hours, cooled and filtered. N-Piperidylsulphamide (1.64 g) was added to the filtrate which was heated under reflux for 24 hours. The mixture was concentrated and purified by chromatography to give the title compound.

EXAMPLE 16

1,3-bis-[N'-Hydroxy-N''-(2-(5-methyl-4-imidazolylmethylthio) ethyl)guanidino]propane (a) Dry hydrogen chloride was bubbled through a solution of 1,3-bis-[N'-(2-(5-methyl-4-imidazolylmethylthio)ethyl) thioureido]propane in methanol at 80° for 12 hours, and the solvent was removed to give 1,3-bis[S-methyl-N'-(2-(5-methyl-4-imidazolylmethylthio)ethyl)isothioureido]propane tetrahydrochloride.

(b) The bis-isothiourea prepared above was treated with hydroxylamine hydrochloride and potassium hydrogen carbonate in dry dimethylformamide at 85° under an atmosphere of nitrogen to yield the title product.

EXAMPLE 17

1,3-bis-[N'-Methyl-N''-(2-(5-methyl-4-imidazolylmethylthio)ethyl) guanidino]propane 1,3-bis-[S-Methyl-N'-(2-(5-methyl-4-imidazolylmethylthio)ethyl) isothioureido]propane tetrahydrochloride was heated with methylamine in methanol to give the title product.

EXAMPLE 18

Substitution of
(a) 4-bromo-5-[(2-aminoethyl)thiomethyl]imidazole
(b) 4-[(2-aminoethyl)thiomethyl]imidazole
(c) 2-[(2-aminoethyl)thiomethyl]thiazole
(d) 3-[(2-aminoethyl)thiomethyl]isothiazole
(e) 3-chloro-2-[(2-aminoethyl)thiomethyl]pyridine
(f) 3-hydroxy-2-[(2-aminoethyl)thiomethyl]pyridine
(g) 3-methyl-2-[(2-aminoethyl)thiomethyl]pyridine for 4-methyl-5-((2-aminoethyl)thiomethyl)imidazole in the procedure of Example 1(a) followed by treatment of the product according to the general procedure of Examples 1(b) and 2 gave
(a) 1,3-bis[N'-(2-(5-bromo-4-imidazolylmethylthio)ethyl) thioureido]propane
(b) 1,3-bis[N'-(2-(4-immidazolylmethylthio)ethyl) thioureido]propane
(c) 1,3-bis[N'-(2-(2-thiazolylmethylthio)ethyl)thioureido]propane
(d) 1,3-bis[N'-(2-(3-isothiazolylmethylthio)ethyl)thioureido]propane
(e) 1,3-bis[N'-(2-(3-chloro-2-pyridylmethylthio)ethyl)thioureido]propane
(f) 1,3-bis[N'-(2-(3-hydroxy-2-pyridylmethylthio)ethyl)thioureido]propane

EXAMPLE 19

Substitution of the following amines:
(a) 2-[2-aminopropylthio]oxazole
(b) 3-[(2-aminoethyl)thiomethyl]isoxazole
(c) 3-[(2-aminoethyl)thiomethyl]pyrazole
(d) 3-[(2-aminoethyl)thiomethyl]-1,2,4-triazole
(e) 5-amino-2-[(2-aminoethyl)thiomethyl]-1,3,4-thiadiazole
(f) 2-[(2-aminoethyl)thiomethyl]pyrimidine
(g) 2-[(2-aminoethyl)thiomethyl]pyrazine
(h) 3-[(2-aminoethyl)thiomethyl]pyridazine
(i) 1-methyl-2-[(2-aminoethyl)thiomethyl]imidazole
(j) 2-[(2-aminoethyl)thiomethyl]imidazole
for 4-methyl-5-((2-aminoethyl)thiomethyl)imidazole in the procedure of Example 1(a) followed by treatment of the products according to the general procedure of Examples 1(b) and 2 results in the production of the following products
(a) 1,3-bis[N'-(2-(2-oxazolylthio)propyl)thioureido]propane
(b) 1,3-bis[N'-(2-(3-isoxazolylmethylthio)ethyl)thioureido]propane
(c) 1,3-bis[N-(2-(3-pyrazolylmethylthio)ethyl)thioureido]propane
(d) 1,3-bis[N-(2-(3-(1,2,4-triazolyl)methylthio)ethyl)thioureido]propane
(e) 1,3-bis[N-(2-(5-amino-2-(1,3,4-thiadiazolyl)methylthio)ethyl)thioureido]propane
(f) 1,3-bis[N-(2-(2-pyrimidylmethylthio)ethyl)thioureido]propane
(g) 1,3-bis[N'-(2-(2-pyrazolylmethylthio)ethyl)thioureido]propane
(h) 1,3-bis[N'-(2-(3-pyridazolylmethylthio)ethyl)thioureido]propane
(i) 1,3-bis[N'-(2-(1-methyl-2-imidazolylmethylthio)ethyl)thioureido]propane
(j) 1,3-bis[N'-(2-(2-imidazolylmethylthio)ethyl)thioureido]propane

EXAMPLE 20

(a) (i) A solution of 4-(2-aminoethyl)thiomethyl-)imidazole (6.0 g) and benzoyl isothiocyanate (6.0 g) in chloroform (150 ml) was heated under reflux for one hour. Concentration followed by recrystallisation from ethyl acetate-isopropyl acetate afforded N-benzoyl-N'-(2-(4-imidazolylmethylthio)ethyl)thiourea (7.5 g). An analytically pure sample (from aqueous isopropyl alcohol) had m.p. 126°–128°.

(ii) The benzoyl thiourea (6.0 g) was added to a solution of potassium carbonate (1.4 g) in water (80 ml) at 60°. The solution was maintained at this temperature for one hour, concentrated to low bulk and acidified with hydrochloric acid. Benzoic acid was removed by filtration and the filtrate was basified with potassium carbonate and concentrated under reduced pressure. Following extraction with isopropyl alcohol and concentration, the product was crystallised from isopropyl acetate. Recrystallisation from water gave N-(2-(4-imidazolylmethylthio)ethyl)thiourea (2.5 g) m.p. 135°7°.

(Found: C, 38.9; H, 5.5; N, 26.1; S, 29.6; $C_7H_{12}N_4S_2$ requires: C, 38.9; H, 5.6; N, 25.9; S, 29.6%)

(b) Substitution of
(a) 4-bromo-5-[(2-aminoethyl)thiomethyl]imidazole
(b) 4-[(2-aminoethyl)thiomethyl]imidazole
(c) 2-[(2-aminoethyl)thiomethyl]thiazole
(d) 3-[(2-aminoethyl)thiomethyl]isothiazole
(e) 3-chloro-2-[(2-aminoethyl)thiomethyl]pyridine
(f) 3-hydroxy-2-[(2-aminoethyl)thiomethyl]pyridine
(g) 3-methyl-2-[(2-aminoethyl)thiomethyl]pyridine
for 4-(2-aminoethyl)thiomethyl)imidazole in the above procedure and treatment of the products according to the general procedure of Example 5 gives
(a) 1,3-bis[N'-(2-(5-bromo-4-imidazolylmethylthio)ethyl)guanidino]propane
(b) 1,3-bis[N'-(2-(4-imidazolylmethylthio)ethyl)guanidino]propane
(c) 1,3-bis[N'-2-(2-thiazolylmethylthio)ethyl)guanidino]propane
(d) 1,3-bis[N'-(2-(3-isothiazolylmethylthio)ethyl)guanidino]propane
(e) 1,3-[N'-(2-(3-chloro-2-pyridylmethylthio)ethyl)guanidino]propane
(f) 1,3-bis[N'-(2-(3-hydroxy-2-pyridylmethylthio)ethyl)guanidino]propane

EXAMPLE 21

Treatment of
(a) 2-[2-aminopropylthio]oxazole
(b) 3-[(2-aminoethyl)thiomethyl]isoxazole
(c) 3-[(2-aminoethyl)thiomethyl]pyrazole
(d) 3-[(2-aminoethyl)thiomethyl]-1,2,4-triazole
(e) 2-[(3-aminopropylthio)pyrimidine
(f) 2-[(2-aminoethyl)thiomethyl]pyrazine
(g) 3-[(2-aminoethyl)thiomethyl]pyridazine
(h) 1-methyl-2-[(2-aminoethyl)thiomethyl]imidazole
(i) 2-[(2-aminoethyl)thiomethyl]imidazole
according to the general procedure of Example 20 gives
(a) 1,3-bis[N'-(2-(2-oxazolylthio)propyl)guanidino]propane
(b) 1,3-bis[N'-(2-(3-isoxazolylmethylthio)ethyl)guanidino]ppropane
(c) 1,3-bis[N'-(2-(3-pyrazolylmethylthio)ethyl)guanidino]propane
(d) 1,3-bis[N-(2-(3-(1,2,4-triazolyl)methylthio)ethyl)guanidino]propane
(e) 1,3-bis[N-(3-(2-pyrimidylthio)propyl)guanidino]propane
(f) 1,3-bis[N'-(2-(3-pyrazolylmethylthio)ethyl)guanidino]propane
(g) 1,3-bis[N'-(2-(3-pyridizylmethylthio)ethyl)guanidino]propane
(h) 1,3-bis[N'-(2-(1-methyl-2-imidazolylmethylthio)ethyl)guanidino]propane
(i) 1,3-bis[N'-(2-(2-imidazolylmethylthio)ethyl)guanidino]propane

EXAMPLE 22

Substitution of
(a) 4-(4-aminobutyl)imidazole
(b) 4-(4-aminobutyl)-5-methylimidazole
(c) 4-(4-aminobutyl)-5-bromoimidazole
(d) 4-(4-aminobutyl)thiazole
for 4-methyl-5-((2-aminoethyl)thiomethyl)imidazole in the procedure of Example 1(a) followed by treatment of the product according to the general procedure of Examples 1(b) and 2 gave
(a) 1,3-bis-[N'-4-(4-imidazolylbutyl)thioureido]propane
(b) 1,3-bis-[N'-4-(5-methyl-4-imidazolylbutyl)thioureido]propane
(c) 1,3-bis-[N'-4-(5-bromo-4-imidazolylbutyl)thioureido]propane
(d) 1,3-bis-[N'-4-(4-thiazolylbutyl)thioureido]propane

EXAMPLE 23

Treatment of
(a) 4-(4-aminobutyl)imidazole
(b) 4-(4-aminobutyl)-5-methylimidazole
(c) 4-(4-aminobutyl)-5-bromoimidazole
(d) 4-(4-aminobutyl)thiazole
according to the general procedure of Example 20 gives
(a) 1,3-bis[N'-4-(4-imidazolylbutyl)guanidino]propane
(b) 1,3-bis-[N'-4-(5-methyl-4-imidazolylbutyl)guanidino]propane
(c) 1,3-bis-[N'-4-(5-bromo-4-imidazolylbutyl)guanidino]propane
(d) 1,3-bis-[N'-4-(4-thiazolylbutyl)guanidino]propane

EXAMPLE 24

1-[N'-(2-(5-Methyl-4-imidazolylmethylthio)ethyl)-guanidino[-3-[N'-(2-(2-thiazolylmethylthio)ethyl)thioureido]propane (a) (i) 3-Benzoylaminopropylamine was treated successively with carbon disulphide and methyl iodide according to the general procedure of Example 1 (a) (b) to give S-methyl-N-(3-benzoylaminopropyl)dithiocarbamate hydriodide (ii) The above hydriodide was treated with one equivalent of sodium ethoxide and 2[(2-aminoethyl)thiomethyl]thiazole, and the product was hydrolysed with acid to give N-(3-aminopropyl)-N'-(2-(2-thiazolylmethylthio)ethyl)thiourea (iii) The above thiourea was heated under reflux for 2 hours with an aqueous solution of S-methyl-N-[2-((5-methyl-4-imidazolyl)methylthio)ethyl]thiouronium sulphate in water. The mixture was concentrated and purified by chromatography to give the title compound.

(b) (i) 2-[(2-Aminoethyl)thiomethyl]]thiazole was successively treated with carbon disulphide and methyl iodide according to the general procedure of Example 1 (a)(b) to give S-methyl-N-[2-(2-thiazolylmethylthio)ethyl]dithiocarbamate hydriodide.

(ii) The above hydriodide was treated with one equivalent of sodium ethoxide and 3-benzoylaminopropylamine and the product was hydrolysed with acid, and subjected to the procedure (a) (iii) above, to give the title compound.

EXAMPLE 25

1,3-bis-[N'-(2-(4-imidazolylethylthio)ethyl)guanidino]propane

When 4-[2-(2-aminoethyl)thioethyl]imidazole is subjected to the general procedure of Example 20 the title compound is produced.

EXAMPLE 26

1,3-bis-[N'-Carbamoyl-N'''-(2-(5-methyl-4-imidazolylmethylthio)ethyl)guanidino]propane Treatment of 1,3-bis-[N'-cyano-N'''-(2-(5-methyl-4-imidazolylmethylthio)ethyl)guanidino]propane with dilute hydrochloric acid at 40° yielded the title product.

EXAMPLE 27

1,3-bis-[1-[2-((5-Methyl-4-imidazolyl)methylthio)ethylamino]-2-nitrovinylamino]propane A solution of 1-nitro-2-methylthio-2-[2-(5-methyl-4-imidazolyl)methylthio)ethylamino]ethylene (2.0 g) and 1,3-diaminopropane (0.26 g) in ethanol (10 ml) was heated under reflux for 2 hours. The product was purified on an ion-exchange resin (GC 50 (H+)), by elution with 0.012 N hydrochloric acid and finally chromatographed on a column of silica gel to yield the title compound.

EXAMPLE 28

1-[1-(2-((5-Methyl-4-imidazolyl)methylthio)ethylamino)-2-nitrovinylamino]-3-[N'-cyano-N'''-(2-(2-pyridylmethylthio)ethyl)guanidino]propane 1-Nitro-2-methylthio-2-[2-((5-methyl-4-imidazolyl)methylthio)ethylamino]ethylene was reacted with 3-benzoylaminopropylamine and the product was hydrolysed under acidic conditions and reacted with N-cyano-N'[2-(2-pyridylmethylthio)ethyl]-S-methylisothiourea to give the title compound.

EXAMPLE 29

| Ingredients | Amounts |
| --- | --- |
| 1,3-bis-[N'—(2-(5-Methyl-4-imidazolylmethylthio)ethyl)guanidino]propane dihydrochloride | 150 mg. |
| Sucrose | 75 mg. |
| Starch | 25 mg. |
| Talc | 5 mg. |
| Stearic Acid | 2 mg. |

The ingredients are screened, mixed and filled into a hard gelatin capsule.

| Ingredients | Amounts |
| --- | --- |
| 1,3-bis-[N'—(2-(5-Methyl-4-imidazolylmethylthio)ethyl)guanidino]propane dihydrochloride | 200 mg. |
| Lactose | 100 mg. |

The ingredients are screened, mixed and filled into a hard gelatin capsule.

What is claimed is:

1. A compound of the formula:

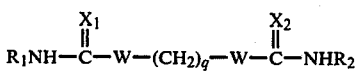

wherein $R_1$ and $R_2$ each represent a grouping of the structure:

wherein Het is a nitrogen containing 5 or 6 membered heterocyclic ring selected from imidazole, thiazole, isothiazole, oxazole, isoxazole, pyrazole, triazole, thiadiazole, pyrimidine, pyrazine or pyridazine which is optionally substituted by lower alkyl, hydroxyl, halogen or amino, except that $R_1$ and $R_2$ are not both selected from thiazole, isothiazole, oxazole, isoxazole, pyrazole or triazole containing groups, and are not both thiadiazole or pyrimidine or pyrazine or pyridazine, and when one of $R_1$ and $R_2$ is an imidazole containing group, the other is not an imidazole, pyrazole or triazole containing group; Z is sulphur or a methylene group; m is 0, 1 or 2; n is 2 or 3 and the sum of m and n is 3, 4 or when Y is other than hydrogen, methyl, or hydroxyl, 2; $X_1$ and $X_2$, which may be the same or different, are each sulphur, $CHNO_2$ or NY wherein Y is hydrogen, hydroxy, lower alkyl, cyano, $CONH_2$ or $SO_2R_3$; $R_3$ is lower alkyl, phenyl, tolyl, trifluoromethyl or amino; W is NH, and when $X_1$ and $X_2$ are NH, W may also be sulphur, and q is an integer from 2 to 8; or a pharmaceutically acceptable acid addition salt thereof.

2. A compound according to claim 1 wherein W is NH.

3. A compound according to claim 2 wherein $X_1$ and $X_2$, which may be the same or different, are each sulphur or NY and wherein Y is defined in claim 1.

4. A compound according to claim 1 wherein Z is sulphur m is 1 and n is 2.

5. A compound according to claim 1 wherein in one of $R_1$ and $R_2$ Het is imidazole, imidazole substituted by methyl or halogen, thiazole, isothiazole, or isothiazole.

6. A compound according to claim 1 wherein $X_1$ and $X_2$ are the same.

7. A compound according to claim 6 wherein $X_1$ and $X_2$ are both sulphur, NH or NCN.

8. A compound according to claim 6 wherein $X_1$ and $X_2$ are both $CHNO_2$.

9. A compound according to claim 1 wherein q is from 2 to 4.

10. A compound according to claim 9 wherein q is 3.

11. A pharmaceutical composition to inhibit H-2 histamine receptors, said H-2 histamine receptors being those histamine receptors which are not inhibited by mepyramine but are inhibited by burimamide, comprising, in an effective amount to inhibit said receptors, a compound of claim 1 in combination with a pharmaceutically acceptable diluent or carrier.

12. A method of inhibiting H-2 histamine receptors, said H-2 histamine receptors being those histamine receptors which are not inhibited by mepyramine but are inhibited by burimamide, which comprises administering orally or parenterally to an animal in need thereof in an effective amount to inhibit said receptors a compound of claim 1.

* * * * *